United States Patent [19]

Kawashima et al.

[11] 3,992,370
[45] Nov. 16, 1976

[54] 1,1-DICHLORO-1A,1B-DIHYDRODIBENZO(B,F)CYCLOPROP(D)AZEPINE-6(1H)-CARBOXALDEHYDE

[75] Inventors: Kenya Kawashima; Takahiro Saraie; Yasuhiko Kawano; Toshihiro Ishiguro, all of Osaka, Japan

[73] Assignee: Takeda Chemical Industries, Ltd., Japan

[22] Filed: Jan. 23, 1974

[21] Appl. No.: 435,965

[30] Foreign Application Priority Data

Feb. 3, 1973 Japan............................. 48-13987

[52] U.S. Cl............................................ 260/239 D
[51] Int. Cl.².................................. C07D 223/22
[58] Field of Search............................ 260/239 D

[56] References Cited
UNITED STATES PATENTS

| | | | |
|---|---|---|---|
| 3,265,743 | 8/1966 | Robinson...................... | 260/618 D |
| 3,658,908 | 4/1972 | Coyne et al.................. | 260/618 D |
| 3,679,662 | 7/1972 | Morita et al................. | 260/239 D |

FOREIGN PATENTS OR APPLICATIONS

| | | | |
|---|---|---|---|
| 2,030,315 | 12/1970 | Germany...................... | 260/239 D |

OTHER PUBLICATIONS

Starks, J.A.C.S., vol. 93, pp. 195–199, (1971).

*Primary Examiner*—Nicholas S. Rizzo
*Assistant Examiner*—D. B. Springer
*Attorney, Agent, or Firm*—Wenderoth, Lind & Ponack

[57] ABSTRACT

1,1-Dichloro-1a,10b-dihydrodibenzo(b,f)cycloprop(d)azepine-6(1H)-carboxaldehyde is produced in good yield through a reaction between a compound of the general formula

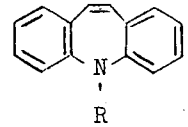

wherein R stands for hydrogen or formyl group and chloroform. Thus obtained product can be used as a valuable intermediate for synthesizing medicines and is further convertible to known drugs, e.g. 6-(3-dimethylamino)propyl)-1, 1a, 6, 10b-tetrahydrodibenzo(b,f)cycloprop(d)azepine.

1 Claim, No Drawings

1,1-DICHLORO-1a,10b-DIHYDRODIBENZO-(b,f)CYCLOPROP(d)AZEPINE-6(1H)-CARBOXALDEHYDE

The present invention relates to a method for producing 1,1-dichloro-1a,10b-dihydrodibenzo(b,f)cycloprop(d)azepine-6(1H)-carboxaldehyde which is a valuable intermediate for a pharmaceutically usable compound e.g. 6-(3-dimethylamino)propyl)-1,1a,6,10b-tetrahydrodibenzo(b,f)cycloprop(d)azepine. More particularly, this invention is directed to the method for producing 1,1-dichloro-1a, 10b-dihydrodibenzo(b,f)cycloprop(d)azepine-6(1H)-carboxaldehyde which comprises reacting a compound of the general formula

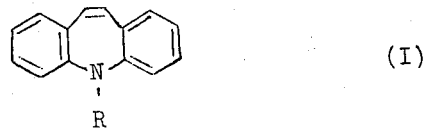

(I)

wherein R stands for hydrogen or formyl group, with chloroform.

Heretofore, 6-(3-(dimethylamino)propyl)-1,1a,6,10b-tetrahydrodibenzo(b,f)cycloprop(d)azepine is prepared by reacting e.g. a 5-alkyl-5H-dibenz(b,f)azepine or 5H-dibenz(b,f)azepine with a carbenoid reagent and the product obtained is oxidized, hydrolyzed and then reacted with 3-chloro-N,N-dimethylpropylamine (U.S. Pat. No. 3,679,662). This method, however, is not fully satisfactory from commercial points of view, for it has some drawbacks; namely, it involves many steps, does not afford good yields and involves the use of dangerous reagents, which might prove hazardous in production runs, or reagents which are expensive.

The intensive research conducted by the present inventors to overcome these disadvantages led to the establishment of the novel method for the production of a novel compound, i.e. 1,1-dichlor-1a,10b-dihydrodibenzo(b,f)cycloprop(d)azepine-6-(1H)-carboxaldehyde which comprises reacting a compound (I) with chloroform. Thus obtained compound may easily be converted e.g. by reduction of it into 1,1a,6,10b-tetrahydrodibenzo(b,f)cycloprop(d)azepine(IV), which is known as an intermediate for producing 6-(3-(dimethylamino)propyl)-1,1a,6,10b-tetrahydrodibenzo(b,f)cycloprop(d)azepine (V) and led to it according to the method described in the above U.S. Pat. No. 3,679,662.

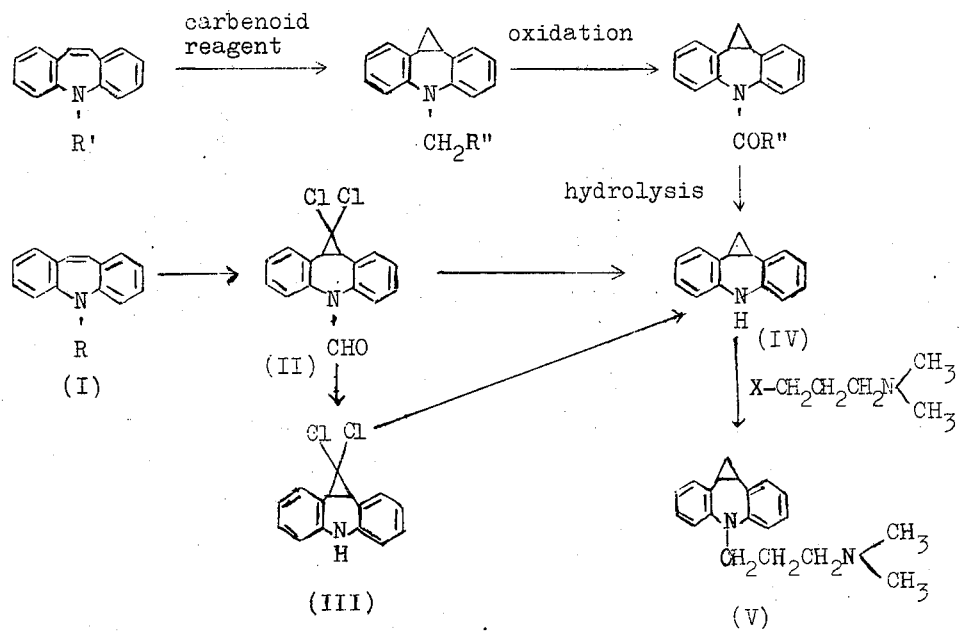

(R has the same meaning as above and R' stands for hydrogen or a radical of —CH₂R" wherein R" stands for hydrogen or alkyl group.)

The reaction of this invention may be conducted in a solvent system comprising an aqueous solution e.g. water and an organic solvent e.g. chloroform, carbon tetrachloride, benzene, toluene, xylene, etc. The reaction is generally carried out at the temperature from 0° C to the boiling point of the solvent, preferably 30° to 50° C. It is desirable to complete the reaction within from 1 hour to 24 hours. The reaction may be accelerated in the presence of a phase-transfer catalyst in the reaction system. Namely, the phase-transfer catalyst promotes a reaction between two substances located in different phases of a mixture by transferring one reactant across the interface into the other phase to facilitate collision of the reactant molecules. The phase-transfer catalysis was first reported in the "Journal of the American Chemical Society" volume 93, page (1971). The phase-transfer catalyst may be a quaternary ammonium salt, such as tetraalkylammonium salt (e.g. tetramethylammonium chloride, cetyltrimethylammonium chloride, tetraethylammonium bromide, diethyldimethylammonium bromide, etc.), aryltrialkylammonium salt (e.g. phenyltrimethylammonium chloride, phenyltriethylammonium bromide, etc.), aralkyltrialkylammonium salt, (e.g. benzyltrimethylammonium chloride, phenethyltrimethylammonium bromide, benzyltriethylammonium chloride, etc.), arylaralkyldialkylammonium salt (e.g. phenylbenzyldimethylammonium chloride, phenylbenzyldiethylammonium bromide, etc.), diaryldialkylammonium salt (e.g. diphenyldimethylammonium chloride, diphenyldiethylammonium bromide, etc.), triarylalkylammonium salt (e.g. triphenylethylammonium chloride, triphenylmethylammonium chloride, etc.), triaralkylalkylammonium salt (e.g. tribenzylmethylammonium chloride, triphenethylethylammonium bromide, etc.), tetraarylammonium salt (e.g. tetraphenylammonium chloride, tetraphenylammonium bromide, etc.), tetraaralkylammonium salt (e.g. tetrabenzylammonium chloride, tetraphenethylammonium bromide, etc.), aryl diaralkylalkylammonium salt (e.g. phenyldibenzylmethylammonium chloride, phenyldiphenethylethylammonium bromide, etc.), diarylaralkylalkylammonium salt (e.g. diphenylbenzylmethylammonium chloride, diphenylphenethylethylammonium bromide, etc.), or a phosphonium salt, such as tetraalkylphosphonium salt (e.g. tetramethylphosphonium chloride, cetyltrimethylphosphonium chloride, tetraethylphosphonium bromide, etc.), aryltrialkylphosphonium salt (e.g. phenyltrimethylphosphonium chloride, phenyltriethylphosphonium bromide, etc.), aralkyltrialkylphosphonium salt (e.g. benzyltrimethylphosphonium chloride, phenethyltriethylphosphonium bromide, benzyltriethylphosphium bromide, etc.), arylaralkyldialkylphosphonium salt (e.g. phenylbenzyldimethylphosphonium chloride, phenylbenzyldiethylphosphonium chloride, phenylphenethyldimethylphosphonium bromide, etc.), diaryldialkylphosphonium salt (e.g., diphenyldimethylphosphonium chloride, diphenyldiethylphosphonium bromide, etc.), triarylalkylphosphonium salt (e.g. triphenylmethylphosphonium chloride, triphenylethylphosphonium bromide, etc.), triaralkylalkylphosphonium salt (e.g. tribenzylmethylphosphonium chloride, triphenethylethylphosphonium bromide, etc.), tetraarylphosphonium salt (e.g. tetraphenylphosphonium, chloride, tetraphenylphosphonium bromide, etc.), tetraaralkylphosphonium salt (e.g. tetrabenzylphosphonium chloride, tetraphenethylphosphonium bromide, etc.), aryldiaralkylalkylphosphonium salt (e.g. phenyldibenzylmethylphosphonium chloride, phenyldiphenethylethylphosphonium bromide, etc.), diarylaralkylalkylphosphonium salt (e.g. diphenylbenzylmethylphosphonium chloride, diphenylphenethylethylphosphonium bromide, etc.) or the like.

The reaction may be progressed in the addition of a base, such as alkali metal hydroxide (e.g. sodium hydroxide, potassium hydroxide, etc.), alkaline earth metal hydroxide (e.g. calcium hydroxide, barium hydroxide, etc.), or the like. In this reaction the chloroform is supposed to form dichloromethylene (:CCl$_2$) which reacts with the compound (I) but can not be isolated. 1,1-Dichloro-1a,10b-dihydrodibenzo(b,f)cycloprop(d)azepine-6(1H)-carboxaldehyde (II) thus produced can easily be purified and isolated by a routine treatment, for example, crystallization, recrystallization, extraction with a solvent, chromatography or the like.

Thus obtained 1,1-dichloro-1a, 10b-dihydrodibenzo(b,f)cycloprop(d)azepine-6(1H)-carboxaldehyde (II) may be reduced to give 1,1a,6,10b-tetrahydrodibenzo(b,f)cycloprop(d)azepine (IV). The reduction may be conducted by a routine reduction procedure, such as catalytic hydrogenation, a process making use of alkali metal, alkaline earth metal, amalgam, etc, with water, alcohol, liquid ammonia, amine, etc. or a process making use of metal hydride, electrolytic reduction. Catalysts usable for the catalytic hydrogenation may be exemplified by a metal such as nickel, platinum, palladium, copper, cobalt, iron, zinc, etc., a metal oxide such as platinum oxide, molybdenum oxide, tungsten oxide, etc., a metal chromate such as copper chromate, zinc chromate, etc., metal chromite such as copper chromite, zinc chromite, etc., a metal sulfide such as tungsten sulfide, molybdenum sulfide, etc. Generally, these catalysts are used with a carrier, for example, silica gel, alumina gel, chromium oxide, diatomaceous earth, activated carbon, activated clay, barium sulfate, calcium carbonate and so on. Alkali metal may be sodium, potassium, lithium, etc. Alkaline earth metal may be calcium, magnesium, etc. Amalgam may be sodium amalgam, aluminum amalgam, etc. Alcohol may be methanol, ethanol, 1-propanol, 2-propanol, butanol, isobutanol, etc. Amine may be alkylamine involving ethylamine, n-propylamine, diisopropylamine, n-butylamine, isobutylamine, sec-butylamine, etc., arylamine involving aniline, diphenylamine, etc., aralkylamine involving benzylamine, dibenzylamine, phenethylamine, etc., alkylarylamine involving N-methylaniline, N-ethylaniline, N-propylaniline, etc., alkylaralkylamine involving N-methylbenzylamine, N-ethylphenethylamine, N-propylbenzylamine, etc., arylaralkylamine involving N-phenylbenzylamine, etc., cycloalkylamine involving cyclopentylamine, cyclohexylamine, etc., cyclic amine involving pyrrolidine, piperidine, etc. or the like. Metal hydride may be lithium aluminum hydride, diethylaluminum hydride, sodium aluminum hydride, sodium borohydride, etc.

Generally the use of alkali metal in liquid ammonia or amine may give the best result in these procedures. For example, 1,1a, 6,10b-tetrahydrodibenzo(b,f)cycloprop(d)azepine (IV) can be obtained in a high yield by the reaction using sodium in liquid ammonia at a temperature of −60° C to the boiling point of ammonia for 30 minutes. The reaction may generally be carried out at the temperature from −80° to 150° C. It is desirable to complete the reaction within from 10 minutes to 24 hours.

The reduction involving the use of sodium with amine is a very profitable procedure, for it has the advantage that the reaction, even at room temperature, can afford 1,1a,6,10b-tetrahydrodibenzo(b,f)cycloprop(d)azepine (IV) in a high yield. The isolation of this compound can be carried out by a routine treatment.

Alternatively, the compound (II) is hydrolyzed to obtain 1,1-dichloro-1,1a,6,10b-tetrahydrodibenzo(b,f)cycloprop(d)azepine (III) and then reduced in the same manner as above. The hydrolysis can be easily performed in the presence of a base, such as alkali metal hydroxide (e.g. sodium hydroxide, potassium hydroxide, etc.), alkali metal carbonate (e.g. sodium carbonate, potassium carbonate, etc.) or the like. The reaction may desirably be conducted in a solvent which may be alcohols, for example, methanol, ethanol, 1-propanol, 2-propanol or butanol. If desirable, the resultant reaction mixture may be subjected after purification to the next reducing reaction, of which conditions are similar to those mentioned above.

The NMR spectra in the examples to be given hereinafter were obtained using a spectrometer Varian T-60 or NH-100. The chemical shifts were expressed in p.p.m. relative to internal tetramethylsilane ($\delta$). Unless otherwise specified, deuteriochloroform was used as the solvent. The symbol $s$ signifies a singlet, $m$ a multiplet and J a coupling constant in Herz.

It is to be understood that the following examples are solely for the purpose of illustration and not to be construed as limitations of this invention, and that many variations may be resorted to without departing from the spirit and scope of this invention. In this specification, "g.", "ml.", "m.p." and "decomp." are "gram", "milliliter", "melting point" and "decomposed", respectively. Temperatures are all uncorrected, and percentages are all on the weight basis.

EXAMPLE 1

At 40° C, 14.48 g. (0.075 mole) of 5H-dibenz(b,f)azepine, 0.57 g. (0.0023 mole) of benzylphenyldimethylammonium chloride, 538 g. (4.5 moles) of chloroform and 360 g. of a 33 % aqueous solution of sodium hydroxide (3.0 moles) are stirred together for 6 hours, after which time 216 g. (5.4 moles) of solid sodium hydroxide and 60 g. of water are added. The mixture is stirred at 40° C for 16 hours and the resulting solution is extracted with chloroform. The chloroform extract is washed with water and dried with anhydrous sodium sulfate, followed by distillation of the solvent to dry up under reduced pressure. The residue is then recrystallized from benzene to give 1,1-dichloro-1a,10b-dihydrodibenzo(b,f)cycloprop(d)azepine-6(1H)-carboxaldehyde in a yield of 77.5 % (17.67 g.). Melting point 213° C(decomp.)

Elemental analysis for $C_{16}H_{11}NOCl_2$: Calcd.: C, 63,18; H, 3.65; N, 4.61. Found: C, 63.28; H, 3.64; N, 4.58.

Nuclear magnetic resonance spectrum (in $CDCl_3$, $\delta$, ppm.): 3.35(s,2H), 7.25–7.65(m,8H), 8.53(s,1H).

EXAMPLE 2

In a procedure similar to Example 1, 0.52 g. (0.0023 mole) of benzyltriethylammonium chloride is used instead of benzylphenyldimethylammonium chloride, whereby 15.83 g. (yield 69.4 %) of 1,1-dichloro-1a,10b-dihydrodibenzo(b,f)cycloprop(d)azepine-6(1H)-carboxaldehyde is obtained. The melting point, elemental analysis and nuclear magnetic resonance spectrum of this compound are in good agreement with those of the compound obtained in Example 1.

EXAMPLE 3

To a solution comprising 4.42 g. (0.02 mole) of 5H-dibenz(b,f)azepine-5-carboxaldehyde, 0.10 g. (0.0006 mole) of tetraethylammonium chloride and 143.2 g. (1.2 mole) of chloroform, there is added 128 g. (1.6 mole) of a 50 % aqueous solution of sodium hydroxide. The mixture is stirred at 40° C for 3 hours and the resulting solution is extracted with chloroform. The chloroform extract is washed with water and dried with anhydrous sodium sulfate, followed by distillation of the solvent under reduced pressure. The resultant crude product is then recrystallized from benzene to give 3.70 g. (61.0 %) of 1,1-dichloro-1a,10b-dihydrodibenzo(b,f)cycloprop(d)azepine-6(1H)-carboxaldehyde which is identical with the compound obtained in Example 1, by melting point and elemental analysis.

EXAMPLE 4

At 50° C, a solution comprising 18.25 g. (0.06 mole) of 1,1-dichloro-1a,10b-dihydrodibenzo(b,f)cycloprop(d)azepine-6(1H)-carboxaldehyde, 16.8 g. (0.42 mole) of sodium hydroxide and 319 g. of ethanol is stirred for 4.5 hours and, then, the reaction mixture is neutralized with conc. HCl. Ethanol is distilled off, water is added and extracted with ethyl acetate. The ethyl acetate extract is washed with water and dried with anhydrous sodium sulfate, followed by the distillation of the solvent to dry up under reduced pressure. The residue is then recrystallized from benzene to give 12.0 g. (yield 7.30 %) of 1,1-dichloro-1,1a,6,10b-tetrahydrodibenzo(b,f)cycloprop(d)azepine. Melting point: 162°–163° C Elemental analysis for $C_{15}H_{11}NCl_2$: Calcd.: C, 65.23; H, 4.02; N, 5.07. Found: C, 65.52; H, 3.77; N, 4.82.

Nuclear magnetic resonance spectrum (in $CDCl_3$, $\delta$, ppm.): 3.26(s,2H), 5.60(broad, 1H), 6.70–7.54(m,8H).

EXAMPLE 5

In 20 ml. of liquid ammonia is suspended 1.824 g. of 1,1-dichloro-1a,10b-dihydrodibenzo(b,f)cycloprop(d)azepine-6(1H)-carboxaldehyde, and while the suspension is stirred at −40° to −50° C, 0.69 g. of small pieces of sodium metal are added. The system is stirred at the same temperature for 1 hour, after which time 1.5 g. of ammonia chloride is added. The liquid ammonia is distilled off and 20 ml. of water is added. The mixture is extracted three times with 20 ml. portions of benzene and the extracts are washed with water and dried. The benzene extracts are passed over a column packed with silica gel and then adsorbed material is eluted by means of a mixed solvent of benzenecyclohexane (6:4). The eluate is concentrated, whereby 0.658 g. (53 %) of 1,1a,6,10b-tetrahydrodibenzo(b,f)cycloprop(d)azepine is obtained.

EXAMPLE 6

In 20 ml. of liquid ammonia is suspended 1.104 g. of 1,1-dichloro-1,1a,6,10b-tetrahydrodibenzo(b,f)cycloprop(d)azepine and while the suspension is stirred at −40° to −50° C, 0.46 g. of small pieces of sodium metal is added. The system is stirred at the same temperature for 1 hour, after which time 1.0 g. of ammonium chloride is added. The liquid ammonia is distilled off and 20 ml. of water is added. The mixture is then extracted three times with 20 ml. portions of benzene and the extracts are washed with water and dried. Then, the benzene is distilled off and the residue is purified by chromatography on a column of silica gel in the same manner described in Example 5. The procedure gives 0.667 g. (80.5%) of 1,1a,6,10b-tetrahydrodibenzo(b,f)cycloprop(d)azepine.

EXAMPLE 7

In 20 ml. of diisopropylamine is suspended 0.552 g. of 1,1-dichloro-1,1a,6,10b-tetrahydrodibenzo(b,f)cycloprop(d)azepine and at room temperature, 0.46 g. of small pieces of sodium metal are added. The system is stirred at the same temperature for 70 hours, after which time the excess sodium metal is decomposed with 10 ml. of methanol. The mixture is poured into 20 ml. of water and extracted three times with 20 ml. portions of benzene. After washing with water and drying, the solvent is distilled off under reduced pressure and the residue is purified by chromatography on a column of silica gel in the same manner as in Example 5. The procedure gives 0.297 g. (71.7 %) of 1,1a,6,10b-tetrahydrodibenzo(b,f)cycloprop(d)azepine.

EXAMPLE 8

In 10 ml. of n-butylamine is dissolved 1.104 g. of 1,1-dichloro-1,1a,6,10b-tetrahydrodibenzo(b,f)cycloprop(d)azepine and while the solution is stirred at room temperature, 0.46 g. of small pieces of sodium metal are added.

The system is stirred at that temperature for 75 hours and the excess sodium metal is decomposed with 12 ml. of methanol. The solution is poured into 20 ml. of water and extracted three times with 20 ml. portions of benzene. After washing with water and drying, the product is purified by chromatography on a column of silica gel at the same manner described in Example 5. The above procedure gives 0.53 g. (64 %) of 1,1a,6,10b-tetrahydrodibenzo(b,f)cycloprop(d)azepine.

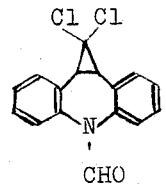

What we claim is:
1. Compound of the formula